(12) United States Patent
Karakasoglu

(10) Patent No.: US 6,290,654 B1
(45) Date of Patent: Sep. 18, 2001

(54) OBSTRUCTIVE SLEEP APNEA DETECTION APPARATUS AND METHOD USING PATTERN RECOGNITION

(75) Inventor: Ahmet Karakasoglu, San Francisco, CA (US)

(73) Assignee: Sleep Solutions, Inc., Palo Alto, CA (US)

( * ) Notice: Subject to any disclaimer, the term of this patent is extended or adjusted under 35 U.S.C. 154(b) by 0 days.

(21) Appl. No.: 09/169,781

(22) Filed: Oct. 8, 1998

(51) Int. Cl.$^7$ ........................................................ A61B 5/08
(52) U.S. Cl. ........................ 600/529; 600/532; 600/538; 128/201.23
(58) Field of Search ..................................... 600/300, 459, 600/481–486, 500–508, 529–538; 128/897–898

(56) References Cited

U.S. PATENT DOCUMENTS

| | | |
|---|---|---|
| 4,129,125 | 12/1978 | Lester et al. . |
| 4,862,144 | 8/1989 | Tao . |
| 4,956,867 | 9/1990 | Zurek et al. . |
| 5,385,144 | 1/1995 | Yamanishi et al. . |
| 5,522,382 * | 6/1996 | Sullivan et al. ................. 128/204.23 |
| 5,853,005 * | 12/1998 | Scanlon ................................ 600/459 |

* cited by examiner

Primary Examiner—John P. Lacyk
Assistant Examiner—Michael Astorino
(74) Attorney, Agent, or Firm—Flehr Hohbach Test Albritton & Herbert LLP

(57) ABSTRACT

Apparatus for detecting a breath pattern of a breathing patient having lungs and a nose and mouth in communication with the lungs and breathing through the nose and/or mouth and creating an airflow into and out of the lungs. The apparatus comprises a sensor in close proximity to the face of the patient for detecting said airflow to provide a first channel of airflow information in an analog format. An analog-to-digital converter is provided for converting the first channel of airflow information in an analog format to a first channel of airflow information in a digital format. A filter is provided for filtering the airflow information in a digital format in the first channel of information to improve the signal-to-noise ratio of the signal to provide filtered airflow information. An estimated volume airflow estimator operates on the filtered airflow information for estimating the amount of air volume inhaled and exhaled by the patient to provide a signal representing the estimated volume of air. A wavelet transform feature extractor is provided for obtaining a continuous-time wavelet transform of the estimated volume of air for ascertaining whether a breathing pattern has been recognized and providing a breathing pattern signal. A neural network pattern recognizer operates on the breathing pattern signal to ascertain when disordered breathing is occurring and provides a disordered breathing signal. A pattern classifier operates on the disordered breathing signal to separate the disordered breathing into apnea and hypopnea categories.

16 Claims, 3 Drawing Sheets

OBSTRUCTIVE SLEEP APNEA DETECTION APPARATUS AND METHOD USING PATTERN RECOGNITION

This invention relates to an obstructive sleep apnea detection apparatus method utilizing pattern recognition.

In application Ser. No. 08/472,441 filed on Jun. 7, 1995 there is disclosed a sleep apnea screening and/or detecting apparatus and method, which has been found to have many desirable features. However, there are limitations in the apparatus and method, particularly where shallow breathing sounds are being monitored. Also, in certain situations there has been difficulty in eliminating background noise or reducing it to a sufficiently low level. There is therefore a need for a new apparatus and method which overcomes these difficulties.

In general, it is an object of the present invention to provide an obstructive sleep apnea detection apparatus and method which utilizes pattern recognition to make it possible to monitor shallow and wide ranges of airflows of the patient producing various sound levels and/or vibration caused by turbulence in the airflow.

Another object of the invention is to provide an apparatus and method of the above character which makes possible unattended home studies of obstructive sleep apnea and hypopnea.

Another object of the invention is to provide an apparatus and method of the above character which only utilizes airflow and/or oxygen saturation sound information for detecting disordered breathing events.

Another object of the invention is to provide an apparatus and method of the above character in which a single vibration sensor can be utilized for measuring turbulence in airflow.

Another object of the invention is to provide an apparatus and method of the above character which may only require the use of a single microphone for picking up the desired signal and ambient noise.

Another object of the invention is to provide an apparatus and method of the above character in which the noise component is eliminated internally in software to provide improved noise cancellation, especially for periodic noises.

Additional objects and features of the invention will appear from the following description in which the preferred embodiments are set forth in detail in conjunction with the accompanying drawings.

In general the apparatus for detecting a breath pattern of a breathing patient having lungs and a nose and mouth in communication with the lungs and breathing through the nose and/or mouth and creating an airflow into and out of the lungs is comprised of a first sensor in close proximity to the face of the patient for monitoring the airflow to provide a first channel of airflow information in an analog format. Analog-to-digital conversion means is provided for converting the first channel of airflow information in an analog format into a first channel of airflow information in a digital format. Means is provided for filtering the airflow in the digital format in the first channel of information to improve the signal-to-noise ratio of the signal to provide filtered airflow information. Means operates on the filtered airflow information for estimating the amount of airflow volume inhaled and exhaled by the patient to provide a signal representing the estimated volume of air. A wavelet transform feature extractor is provided to obtain a continuous time wavelet transform of the estimated volume of air for ascertaining whether a breathing pattern has been recognized and providing a breathing pattern signal. A neural network pattern recognizer operates on the breathing pattern signal to ascertain when disordered breathing is occurring and providing a disordered breathing signal. Means operates on the disordered breathing signal to separate the disordered breathing into apnea and hypopnea categories.

Figure 1:
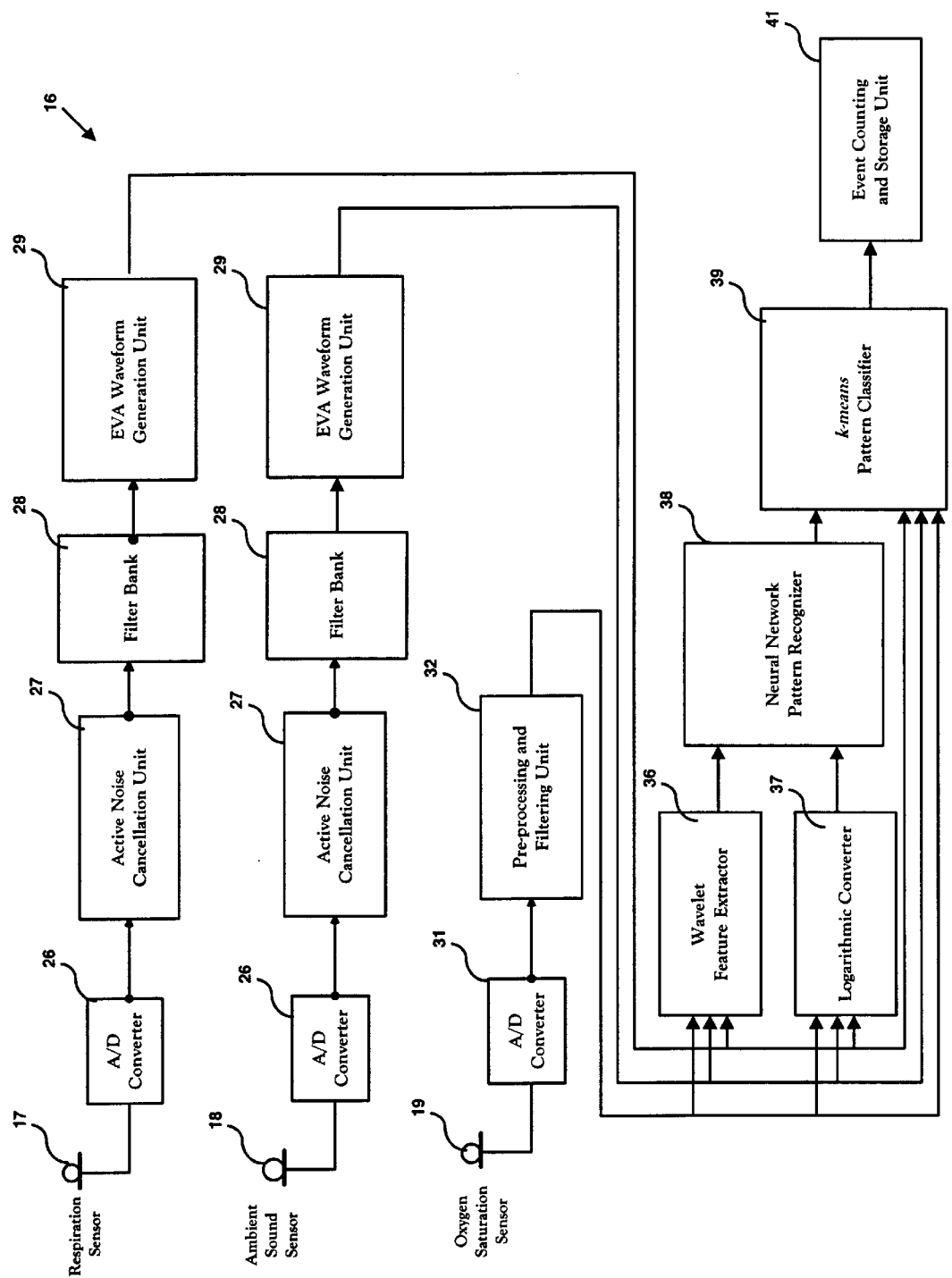
FIG. 1 is a block diagram of an obstructive sleep apnea detection apparatus incorporating the present invention and showing overall system architecture.

More specifically, the obstructive sleep apnea detection apparatus 16 incorporating the present invention is shown in block diagram form in FIG. 1 and as shown consists of an aerial microphone 17 which is utilized to sense breathing or snoring sounds of the patient to provide a first channel of input information. The microphone 17 is located anywhere between 0–2 feet from the patient's head. Additional sound information for a second channel of input information is obtained from a suitable source such as a tracheal microphone 18 located on the patient's neck externally of the patient's trachea. Alternatively, the microphone 18 can be used for picking up ambient sound.

The microphone 17 in the alternative can be a piezoelectric vibration sensor which is immune to sound and thus eliminates the need for the ambient sound sensor 18. The sensor 18 thus senses turbulence in the airflow of the breathing person. A third channel of input information can be received from an oxygen saturation sensor 19 which is positioned on an appropriate location on the body of the patient, such as an earlobe or a finger.

Audible sound signals from the body of the patient are converted by the microphones 17 and 18 to electrical signals which are supplied to two parallel circuits 21 and 22 as shown in FIG. 1 with each parallel circuit consisting of an analog-to-digital (A/D) converter 26. The output from the A/D converter 26 is supplied to an active noise cancellation unit 27 in which background noise is suppressed and the useful information, i.e., the breathing or snoring sound signals are extracted and supplied to a filter bank 28 in which the signals are band pass filtered to adjust the filter band to a desired signal characteristic to further improve the signal-to-noise ratio. The output from the filter bank 28 is supplied to an estimated volume of airflow (EVA) waveform generation unit 29 which provides an estimate of acoustical energy representing the amount of air volume inhaled and exhaled by the patient to ascertain whether or not the patient's breathing is apneic.

The output from the oxygen saturation sensor 19 is supplied to an A/D converter 31 which supplies its output to a pre-processing filtering unit 32. The outputs from the EVA waveform generation units 29 and the pre-processing filtering unit 32 are supplied in parallel to a wavelet feature extractor 36 and a logarithmic converter 37. The outputs of the extractor 36 and the converter 37 are supplied to a neural network pattern recognizer 38 that has its output supplied to a k-means pattern classifier 39 which also receives the outputs from the EVA waveform generation units 29 and the pre-processing and filtering unit 32, as shown. The output of the k-means pattern classifier is supplied to an events counting and storage unit 41 which records abnormal (apnea) breathing/snoring patterns.

Figure 2A:
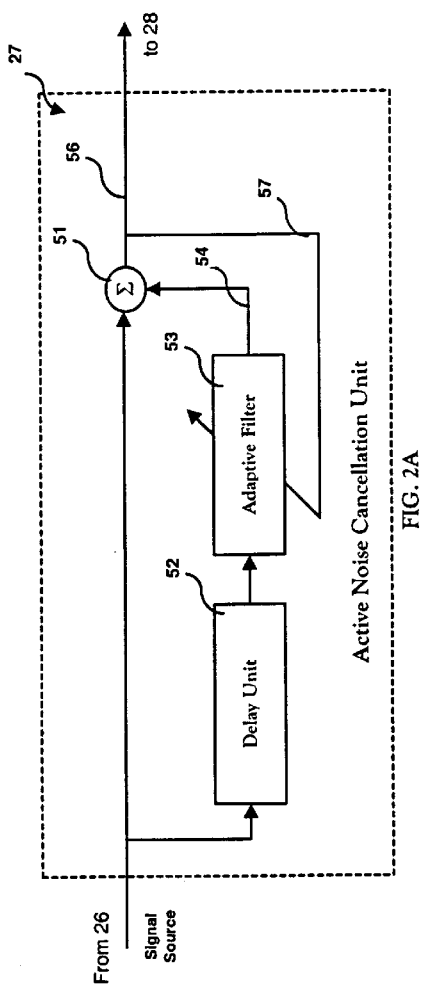
FIG. 2A is a block diagram of an active noise cancellation unit utilized in the obstructive sleep apnea detection apparatus of FIG. 1.

The active noise cancellation unit 27 of FIG. 1 is shown in more detail in FIG. 2A and consists of a single input from the output of the A/D converter 26 identified as a "signal source" which as shown is the microphone 17 that picks up the respiration signal as well as ambient noise. The input to the noise cancellation unit 27 is supplied to a summer or adder 51 and is also supplied to a delay unit 52 which is used to ensure that the active noise cancellation unit 27 will predict future values for the output of the noise cancellation unit 27. The output of the delay unit 52 is supplied to an adaptive linear filter 53 which has its output on line 54 connected to the adder 51. The output from the adder 51 is supplied to an output signal line 56 to the filter bank 26. The output on the output signal line 56 is also supplied by a line 57 connected to the adaptive linear filter 53 to provide an adaptation signal.

The active noise cancellation unit 27 is utilized to remove background noise and operates on the signal supplied by the sensing microphone 17. The adaptive linear filter 28 uses the output signal on the line 56 to produce an estimate of the periodic ambient noise which is in turn subtracted from the sensor output from the sensing microphone 17 in the adder 51. The output on the line 57 is used to adjust the tap weights in the adaptive linear filter 38 to minimize the mean-square value of the overall output on the signal line 56 to cause the overall output to be the best estimate of the desired signal in the minimum mean-square sense.

The adaptive linear filter 28 is in the form of a transversal filter consisting of a set of delay line elements each of which is represented by one sampling period of delay and a corresponding set of adjustable coefficients. At the sampling time instant k, the available signal consists of a set of samples:

$$u(k), u(k-1), u(k-2) \ldots u(k-n)$$

These samples are convolved with a corresponding set of adjustable tap weights:

$$w_1, w_1, w_2 \ldots w_n$$

to produce an output signal sequence, y(n). The signal collected by the breathing/snoring microphone 17 can be designated as d(n). The filter output y(n) is compared with the d(n) to produce an estimation error e(n) which is used by the adaptive algorithm to thereby control the corrections applied to the individual tap weights. This process is continued until the noise estimation error e(n) becomes sufficiently small, as for example $\frac{1}{2}^{16}=1.5\times10^{-5}$. In order to keep the estimation algorithm causal during its operation, an internal time delay, d, supplied by the delay unit 52 is added to the reference input signal supplied by the A/D converter 23. The time duration of d is selected according to the desired sampling rate. When the acoustical properties of the environment in which the microphone 17 is positioned changes, the adaptive algorithm which is used to adjust the coefficients has the added task of continually tracking the variations occurring in the environment being sensed by the microphone 17. For this reason, a normalized adaptation step size, as for example as defined in "Adaptive Signals & Systems" (Widrow & Stearns, Prentice Hall, 1978), has been used to improve the convergence rate for the active noise cancellation unit 27.

Figure 2B:
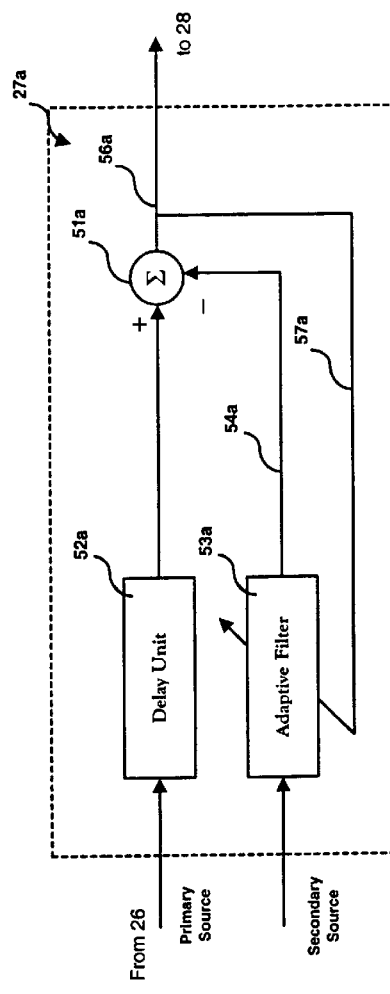
FIG. 2B is an alternative embodiment of an active noise cancellation unit for use in the obstructive sleep apnea detector of FIG. 1.

An alternative active noise cancellation unit 27a is shown in FIG. 2B which is supplied signal and noise information from the first and second input channels provided by the respiration sensor 17 and the ambient sound sensor 18 respectively identified as primary source and secondary source. The signal from the primary source is delivered to the delay unit 52a and thence to the summer or adder 51a. The signal from the secondary source is delivered to the adaptive filter 53a which delivers its output to the summer 51a. The line 57a supplies an adaptation signal to the adaptive filter 53a.

It has been found that the useful portion of the breathing/snoring sound spectrum from human beings is within the frequency band of 200 Hz to 1500 Hz. The filter bank 28 which receives the signal from the active noise cancellation unit 27 consists of a plurality of band pass filters, as for example 13 filters each having a bandwidth of 100 Hz and having cutoff frequencies from 300 Hz to 1500 Hz. When the signal from the active noise cancellation unit 27 arrives at the filter bank 28, a signal is supplied to each of the 13 filters and corresponding outputs are computed. Since the input signals are known, the filter that yields the best signal-to-noise ratio is selected and is used for a predetermined period, as for example, the next three minutes. At the end of this predetermined period, the selection process is repeated in order to accommodate any possible variations in sound characteristics which have occurred.

The filters are realized by using Butterworth's technique.

$$y(k)=a_1y(k-1)+a_2y(k-2)+ \ldots +a_6y(k-6)+b_0u(k)+b_1u(k-1)+ \ldots +b_6u(k-6) \quad \text{Equation 1}$$

For the present application, the $a_i$ and $b_i$ coefficients are calculated using conventional Matlab routines to realize the above-mentioned characteristics for a third order filter.

In order to determine if the patient's breathing is disordered, the amount of air volume inhaled and exhaled by the patient needs to be known. The output from the filter bank 28 supplies a microphone signal which has been processed to remove the artifacts. The EVA waveform generation unit 29 generates a waveform from the air volume inhaled and exhaled by the patient. A scoring methodology is used which closely mimics the results of the methodology of a conventional sleep study involving a standard polysomnograph (PSG). In accordance with the present invention, a prediction sequence has been utilized which generates the estimated volume of airflow (EVA) waveforms which closely follow the actual air volume that is inhaled or exhaled by the patient.

The software code utilized in the present invention implements the following equation to obtain the EVA waveform:

$$\sigma(k)=\alpha_1\sigma(k-1)+\alpha_2\sigma(k-2)+\alpha_3\sigma(k-3)+\beta|x(k)| \quad \text{Equation 2}$$

where k is current sampling instant, k−1 is the previous sampling instant, etc., α(k) is the current estimate of airflow, x(k) is the current microphone sample, α and β are user defined parameters that change the shape of the waveforms. Having $$\alpha_1=0.9, \alpha_2=0.05, \alpha_3=0.03, \alpha_4=0.01 \text{ and } \beta=0.01$$

were suitable choices for obtaining a waveform that closely resembles the airflow waveforms that are obtained by using an airflow meter.

The signal noise from the trachea microphone 18 is treated in a similar manner as the signal and noise from the aerial microphone 17. The information from the oxygen saturation sensor 19 is supplied to the wavelet feature extractor 36 thence to the neural network pattern recognizer 38 and the k-means pattern classifier 39 and the event counting and storage 41 all serve as pattern classification means. The logarithmic pattern converter 37 creates a logarithmic scaling of sound levels. The dynamic range of the signals received from the sensors 17, 18 and 14 is greatly improved by converting the signals received from the sensors 17, 18 and 19 to a logarithmic scale which greatly increases the accuracy of the pattern classification. To obtain a logarithmic scale signal, the EVA signal, f(t) is subjected to the following conversion:

$$d(t) = (1/\log 2) \log[f(t)] = 3.2193 \log [f(t)] \quad \text{Equation 3}$$

Thus, the outputs from the EVA waveform generation units 29 can be identified as f(t) and the output from the logarithmic converter 37 can be characterized as a logarithmic curve, d(t).

The wavelet feature extractor 36 is particularly helpful in analyzing transient signals with short time behavior. The wavelet feature extractor; and 36 forms a continuous-time wavelet transform of the EVA signal f(t) with respect to the wavelet g(t) which is defined as:

$$W_g f(a, b) = \frac{1}{\sqrt{(e)}} \int_{-\infty}^{\infty} f(t) g\left(\frac{t-b}{a}\right) dt \quad \text{Equation 4}$$

where $$g\left(\frac{t-b}{a}\right)$$

is obtained from the mother wavelet g(t) satisfying $$F[g(t)] = G(w); \int_{-\infty}^{\infty} \frac{|G(w)|^2}{|w|} < \infty \quad \text{Equation 5}$$

The wavelet transform (WT) is used as a pre-processor for the neural network pattern classifier 38. The wavelet decomposition of an EVA cycle is used as an input in order to obtain apnea/hypopnea events with respect to time.

Figure 3:
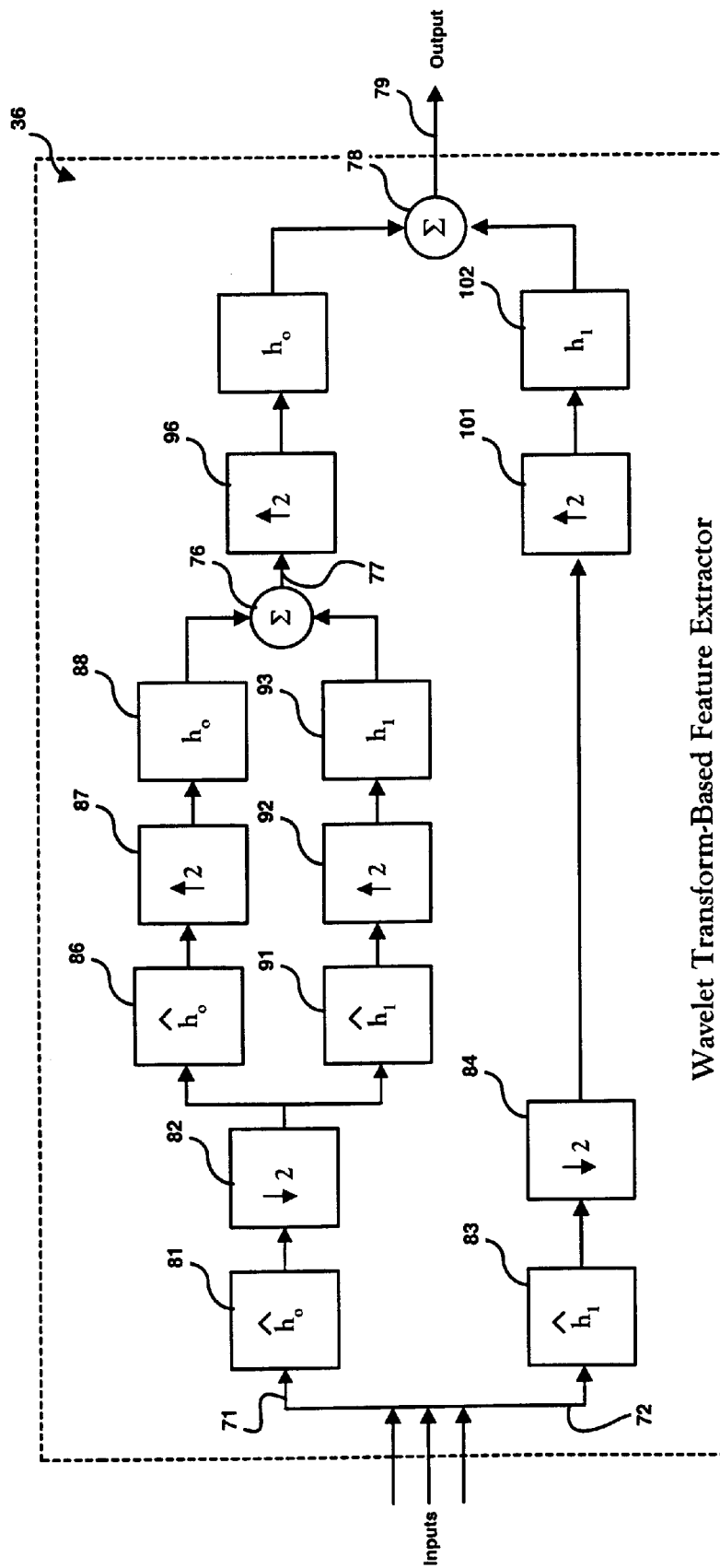
FIG. 3 is a block diagram of a wavelet transform-based feature extractor utilized in the apparatus shown in FIG. 1.

A representation of the wavelet transform-based feature extractor 36 is shown in FIG. 3 and as shown consists of upsampling, downsampling and filtering units. It is adaptive and can be trained to extract breathing events from a breath pattern. As shown, the three inputs to the wavelet transform-based feature extractor as shown in FIG. 3 showing the architecture by which the equations hereinbefore set forth are implemented. As shown, the architecture of the extractor 36 separates the inputs into two frequency bands represented by the upper branch or path 71 and the lower branch or path 72. The upper branch or path is separated into two additional frequency bands represented by branches or paths 73 and 74 which are combined in a summer 76 into a single branch 77 which is combined with the branch 72 and a summer 78 to provide a single output on a line 79. The branch 71 includes an estimated value filter 81 having a symbol therein as indicated and a downsampling estimator 82 having a symbol therein as shown. Similarly the branch 72 has an estimated value filter 83 which feeds into a downsampling estimator 84, both having symbols therein which represent the functions performed thereby.

As pointed out previously the branch 72 divides into two different frequency branches 73 and 74 with the branch 73 having an estimated value filter 86 followed by an upsampling estimator 87 which feeds its output into an actual value filter 88. Similarly the branch 74 is provided with an estimated value filter 91 followed by an upsampling estimator 92 followed by an actual value filter 93. The various components of the branches 73 and 74 are labeled with appropriate indicia to indicate these functions. A branch 77 following the summer 76 is provided with an upsampling estimator 96 followed by an estimated filter value filter 97 which feeds its output into the summer 78. The estimator 84 in the branch 72 supplies its output to an upsampling estimator 101 which feeds its output into an actual value filter 102 which supplies its output to the summer 78.

From the foregoing it can be seen that the input signals are split into two frequency subbands and that the subband signals are processed in the manner shown in FIG. 3 by incrementing or increasing or decrementing or decreasing and processing the frequency bands to obtain the desired information and thereafter combining or reconstructing the signal from the subbands by the use of the summers or adders 76 and 78 respectively.

Thus on the output line 79, there is a full reconstructed signal which has been reconstructed from the subbands as shown in FIG. 3. By providing subbands in multiples of two, it is possible to process information in each frequency subband to obtain the desired hidden information and thereafter to recombine the subbands to provide the signal in its original form. Thus the wavelet transform-based feature extractor rather than operating on the original signal as a whole or total, splits that signal into frequency subbands as hereinbefore described and extracts therefrom disordered breathing events from a given breath pattern or breath signal. Using this extracted information, the neural network-based pattern recognizer analyzes the extracted disordered breathing events to ascertain whether or not apnea or hypopnea have occurred. Thus it can be seen that the combination of the feature extractor 36 and the pattern recognizer 38 ascertain first whether or not there is a breath pattern and secondly if it is a normal breath pattern or apnea or hypopnea. Thus the feature extractor 36 provides the information set and the pattern recognizer ascertains whether or not the information set is a normal breath and if not, whether or not it is apnea or hypopnea.

Figure 4:
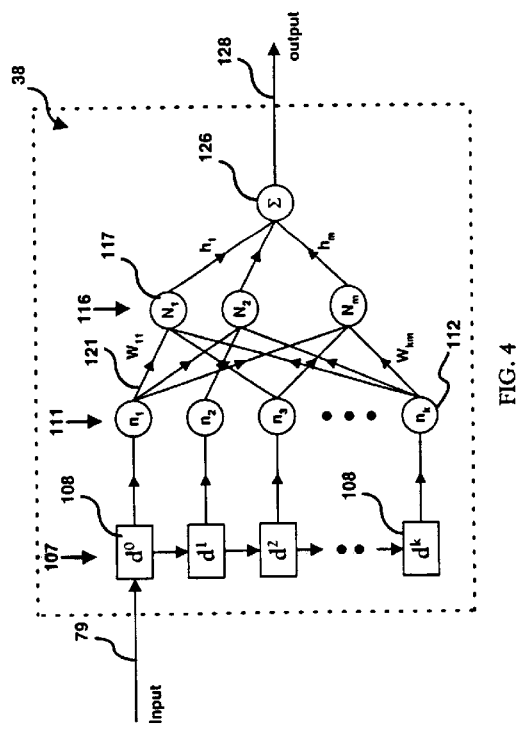
FIG. 4 is a schematic diagram of a neural network-based pattern recognizer utilized in the apparatus shown in FIG. 1.

The pattern recognizer 38 includes an input 79 from the feature extractor 36 and an input 106 from the logarithmic converter 37 which is combined as shown in FIG. 4 into a single input into a delay network 107 consisting of a plurality of individual delays 108 designated $d^0$ standing for zero delay, $d^1$ for a one-step delay, $d^2$ for a two-step delay, up through an infinite number of delays to delay $d^k$. The signals after being delayed in this manner are supplied to a first layer 111 neurons 112 which are weighted from $n_1$ to $n_k$ and are then distributed to a second layer 116 of neurons 117 identified as $N_1$ through $N_m$ through weighted synapsis connectors 121 which are weighted from $W_{11}$ to $W_{km}$. As shown in FIG. 4, the two layers 111 and 116 of neurons are provided to give nonlinearity. The signals after being processed by the second layer 116 are reconstructed with h's, namely $h_1$ through $h_m$ signals to a summer 126 to provide an output on line 127.

The wavelet feature extractor 36 in combination with the neural network pattern recognizer 38 makes possible pattern recognition without the use of preset thresholds. Rather it is an adaptive system which provides a trained or teached network. Thus with the feature extractor 36 and the pattern recognizer 38, the apparatus can be supplied with a few samples of disordered breathing events and from that it learns how to differentiate a healthy breath from a disordered breathing event. As the system or apparatus is trained, the synapses between the layers of neurons are adjusted by adjusting the weights of the synapses. Thus the neural network can readily differentiate between a normal breath signal, an abnormal breath signal, a breath signal with apnea and a breath signal with hypopnea. The system or apparatus of the present invention is capable of adjusting between these patterns. It can readily do this by itself by adaptively adjusting its own synapses.

The neural network can be readily taught by having a technician classify certain breathing events by examining the breathing pattern of one or more patients and classifying the breathing with normal breathing, abnormal breathing and breathing with apnea or breathing with hypopnea. Using this information and supplying the same to the apparatus as shown in FIG. 1, the neural network can be readily trained and thereafter, the neural network need only adapt to each individual's breathing habits which are being monitored.

In the system architecture shown in FIG. 1, the neural network pattern recognizer generally separates the signals into two categories, normal breath versus disordered breath, and the k-means pattern classifier 39 separates the disordered breath into apnea and hypopnea categories. Each event so classified by the pattern classifier 39 is counted in the event counting and storage unit 41.

The logarithmic converter 37 converts the same breathing signal which is received by the wavelet feature extractor 36 and converts the signal to a logarithmic signal. The logarithmic signal is nonlinear and thus can reach saturation and thus in effect acts like a compressor to compress the signal into a smaller variation or narrower range which is not be obtainable from the wavelet feature extractor 36 or the neural network pattern recognizer 38 to thereby provide a more reliable output from the neural network pattern recognizer 38. Thus the neural network pattern recognizer 38 which receives the output from the wavelet feature extractor 36 and the logarithmic converter 37 as shown in FIG. 4. The neural network pattern recognizer 38 consists of nonlinear nodes and convolution units.

The neural network pattern recognizer 38 receives the EVA waveform and information regarding its frequency characteristics and determines if a given sound pattern represents a respiration sound. The neural network pattern recognizer 38 is trained by utilizing known respiration patterns to provide appropriate weights in order to decide if a given sound signal is any kind of breath signal. Directly measured airflow curves and published breathing statistics are utilized in training the neural network pattern recognizer 38.

The k-means pattern classifier 39 is used in conjunction with the neural network pattern recognizer 38. In the k-means pattern classifier 39, the distance of the center of gravity point of each given event with reference events are measured and a decision is made whether the event is (a) a healthy breathing event
(b) a hypopnea event or
(c) an apnea event.

In connection with the classifier 39, the standard polysomniograph decisions were used as reference events when measuring the Euclidian distances which are defined as $$L(t)=[(d_1)^2=(d_2)^2+ \ldots +(d_m)^2]^{1/2} \qquad \text{Equation 6}$$

From the foregoing, it can be seen that there has been provided an obstructive sleep apnea detection apparatus and method using pattern recognition. This pattern recognition makes it possible to monitor shallow and wide ranges of airflow of the patient. The apparatus and method is relatively simple so that it can be utilized in conjunction with unattended home studies. When microphones are used, the noise component is eliminated internally in software to provide improved noise cancellation, particularly for periodic noises.

What is claimed:

1. Apparatus for detecting a breath pattern of a breathing patient having lungs and a nose and mouth in communication with the lungs and breathing through the nose and/or mouth and creating an airflow into and out of the lungs, comprising a first sensor adapted to be placed in close proximity to the patient for monitoring said airflow to provide a first channel of airflow information in an analog format, analog-to-digital conversion means for converting the first channel of airflow information in an analog format into a first channel of airflow information in a digital format, means filtering the airflow information in the digital format in the first channel of information to improve the signal-to-noise ratio of the signal to provide filtered airflow information, means operating on the filtered airflow information for estimating the amount of air volume inhaled and exhaled by the patient to provide a signal representing the estimated volume of air, a wavelet transform feature extractor for providing a continuous-time wavelet transform of the estimated volume of air for ascertaining whether a breathing pattern has been recognized and providing a breathing pattern signal, a neural network pattern recognizer operating on the breathing pattern signal to ascertain when disordered breathing is occurring and providing a disordered breathing signal and means operating on the disordered breathing signal to separate the disordered breathing into apnea and hypopnea categories.

2. Apparatus as in claim 1 wherein said means for monitoring said airflow includes a piezoelectric vibration sensor.

3. Apparatus as in claim 1 wherein said means for monitoring said airflow includes a microphone.

4. Apparatus as in claim 3 further including active noise cancellation means for suppressing background noise in the airflow information in a digital format.

5. Apparatus as in claim 1 further including event counting and storage means for counting apnea and hypopnea events with respect to time.

6. Apparatus as in claim 1 further comprising means for sensing sound in the vicinity of the patient and supplying an analog signal in a second channel, analog-to-digital means for converting the signal in the second channel into a digital format and means for supplying the second channel of digital information to the wavelet feature extractor.

7. Apparatus as in claim 1 further including a logarithmic converter for converting the signal representing the estimated volume of airflow and supplying the same to the neural network pattern recognizer.

8. Apparatus as in claim 1 further comprising an additional sensor for supplying a signal in analog format and analog-to-digital conversion means for converting the signal from the additional sensor and supplying the same to the wavelet feature extractor means.

9. Apparatus as in claim 8 wherein said additional sensor is an oxygen saturation sensor.

10. Apparatus as in claim 1 further including a logarithmic converter for receiving the same information as received by the wavelet transform feature extractor and supplying an output to the neural network pattern recognizer.

11. A method for detecting a breath pattern of a breathing patient having lungs and a nose and a mouth in communication with the lungs and breathing through the nose and/or mouth and creating an airflow into and out of the lungs, comprising detecting said airflow and providing a first channel of airflow information in an analog format, converting the first channel of information in analog format into a digital format, filtering the airflow information in the digital format to improve the signal-to-noise ratio in the airflow information, estimating the air volume inhaled and exhaled by the patient, providing a continuous-line wavelet transform of the estimated volume of air to ascertain when a breathing pattern is being recognized, ascertaining whether the breathing pattern is an abnormal breathing pattern, and classifying the abnormal breathing pattern into apena and hypopnea events.

12. A method as in claim 11 further including the step of recording the apnea and hypopnea events.

13. A method as in claim 11 wherein the airflow is detected by sensing sound.

14. A method as in claim 11 wherein the airflow is detected by sensing a turbulence in the airflow to provide vibrations.

15. A method as in claim 11 further comprising the steps of sensing ambient noise in the vicinity of the patient to provide an analog signal, converting the analog signal to a digital signal in a second channel of information, processing the second channel of information and combining the first channel of information with the second channel of information during the step of providing a continuous-time wavelet transform of the estimated volume of air for ascertaining whether a breathing pattern is being recognized.

16. A method as in claim 11 further comprising the step of logarithmically converting the estimated volume of air and combining that information with the wavelet transform-based feature extraction for providing a continuous-time wavelet transform of the estimated volume of air.

* * * * *